(12) United States Patent
Gustafson

(10) Patent No.: US 6,217,536 B1
(45) Date of Patent: *Apr. 17, 2001

(54) APPARATUS FOR REDUCING MEDIAN NERVE COMPRESSION AND AN ASSOCIATED METHOD

(76) Inventor: Norman P. Gustafson, 2508 Collins Rd., Pittsburgh, PA (US) 15235

( * ) Notice: Subject to any disclaimer, the term of this patent is extended or adjusted under 35 U.S.C. 154(b) by 0 days.

This patent is subject to a terminal disclaimer.

(21) Appl. No.: 08/942,183

(22) Filed: Oct. 1, 1997

Related U.S. Application Data

(63) Continuation-in-part of application No. 08/862,003, filed on May 22, 1997, now Pat. No. 5,919,151.

(51) Int. Cl.⁷ .................................. A61F 5/00; A61F 5/37
(52) U.S. Cl. .............................................. 602/21; 128/879
(58) Field of Search .................................. 602/75, 20, 21, 602/62, 5, 12; 128/878, 879; 606/201–204; 2/16, 20; 473/59–61, 450, 458, 464

(56) References Cited

U.S. PATENT DOCUMENTS

| | | |
|---|---|---|
| 901,830 | 10/1908 | Ramsey . |
| 2,237,252 * | 1/1941 | Longfellow .............................. 602/20 |
| 2,754,825 | 7/1956 | Richmond ............................. 128/327 |
| 3,815,587 | 6/1974 | Guerrant ................................. 128/77 |
| 4,348,023 | 9/1982 | Hinson ................................ 273/29 A |
| 4,441,490 | 4/1984 | Nirschl ................................... 128/77 |
| 4,479,648 * | 10/1984 | Alivo, Jr. ........................... 602/21 X |
| 4,584,993 | 4/1986 | Nelson ................................... 128/77 |
| 4,662,364 * | 5/1987 | Viegas et al. ........................... 602/21 |
| 4,899,763 | 2/1990 | Sebastien et al. .................... 128/878 |
| 5,014,689 | 5/1991 | Meunchen et al. ..................... 128/77 |
| 5,031,640 | 7/1991 | Spitzer ................................. 128/878 |
| 5,160,314 | 11/1992 | Peters ..................................... 602/21 |
| 5,256,136 | 10/1993 | Sucher ................................... 602/21 |
| 5,385,537 * | 1/1995 | Davini ................................ 602/20 X |
| 5,397,296 | 3/1995 | Sydor et al. ............................ 302/21 |
| 5,413,553 | 5/1995 | Downes ................................. 602/21 |

(List continued on next page.)

OTHER PUBLICATIONS

"Anatomic Investigation of the Role of the Lumbrical Muscles in Carpal Tunnel Syndrome" Siegal, et al. *The Journal of Hand Surgery*., pp. 860–836, Sep. 1995.

"Effect of Lumbrical Muscle Incursion Within the Carpal Tunnel on Carpal Tunnel Pressure: A Cadaveric Study", Cobb,M.D., et al., *The Journal of Hand Surgery*, pp. 186–191, Mar. 1995.

*Primary Examiner*—Mickey Yu
*Assistant Examiner*—Denise Pothier

(57) ABSTRACT

Apparatus for applying a generally dorsally directed force to the palm of a person's hand includes an upper structural support which is structured to be secured in generally overlying relationship with respect to the dorsal region of the metacarpals. The upper support has a base structured to be in contact with the hand and support for straps. A palmar compression pad is structured to be in contact with the palm of the hand with the strap or straps being placed in tension to thereby resist undesired movement of the flexor tendon and thereby reduce median nerve compression in the carpal tunnel. In a first embodiment the upper support will have a base, a pair of apertured towers secured to the base through which a strap or straps may pass and a suitable structure for fastening the strap or straps to the upper support. The strap or straps will preferably be adjustably and removably securable to regions adjacent the ends of the palmar compression pad. A bridge may be provided between the upper support towers for facilitating securing the strap or straps thereto. In another embodiment of the invention, the bridge and towers are eliminated. The palmar compression pad is generally rigid and has a pair of generally upwardly extending legs through which one or more straps pass with the upper support secured to the strap. The strap is placed in tension in order to provide the desired dorsally directed force to the palm of the user's hand. Related methods are provided.

18 Claims, 4 Drawing Sheets

U.S. PATENT DOCUMENTS

| | | | |
|---|---|---|---|
| 5,437,620 | 8/1995 | Shelly | 602/21 |
| 5,441,058 * | 8/1995 | Fareed | 602/20 X |
| 5,466,215 | 11/1995 | Lair et al. | 602/21 |
| 5,468,220 | 11/1995 | Sucher | 602/21 |
| 5,478,306 | 12/1995 | Stoner | 602/20 |
| 5,492,133 | 2/1996 | McVicker | 128/876 |
| 5,538,501 * | 7/1996 | Caswell | 602/64 |
| 5,628,723 * | 5/1997 | Grau | 602/53 |
| 5,652,955 * | 8/1997 | Skewis | 602/21 X |
| 5,672,150 * | 9/1997 | Cox | 602/20 X |
| 5,672,151 * | 9/1997 | Calderon-Garcidueñas | 602/20 X |
| 5,771,901 * | 6/1998 | O'Brien | 602/21 X |
| 5,919,151 * | 7/1999 | Gustafson | 602/21 |

\* cited by examiner

APPARATUS FOR REDUCING MEDIAN NERVE COMPRESSION AND AN ASSOCIATED METHOD

CROSS-REFERENCE TO RELATED APPLICATION

This application is a continuation-in-part of U.S. Ser. No. 08/862,003, filed May 22, 1997, U.S. Pat. No. 5,919,151.

BACKGROUND OF THE INVENTION

1. Field of the Invention

The present invention relates to apparatus and an associated method for resisting carpal tunnel syndrome through reduction of median nerve compression in the carpal tunnel.

2. Description of the Prior Art

According to the United States Bureau of Labor Statistics, carpal tunnel syndrome is the number one cause of occupational cumulative trauma injury in the United States. It is also the fastest growing cumulative trauma injury with over 200,000 new cases reported each year in the United States. According to the National Institute of Safety and Health, carpal tunnel syndrome costs are about at $3,000 per case in employee benefits and up to $40,000 per case in direct medical costs. The median job time lost from a case of carpal tunnel syndrome is 20 days according to the Bureau of Labor Statistics.

Numerous strategies have been proposed to treat or prevent carpal tunnel syndrome. Prevention efforts have consisted of modification of work, home, or avocational activities (Ergonomics). Currently, the most widely accepted non-surgical treatments include wrist splinting, non-steroidal anti-inflammatory medication and local steroid injection. The use of ice, massage, acupuncture and electromodalities have also been employed. When conservative treatment is not effective, surgical division of the transverse carpal ligament is typically recommended. Although statistics are not available, the success rate of conservative treatment is not perceived to be great. Surgical treatment is not always effective and can lead to post-surgical problems, such as reflex sympathetic dystrophy.

Examples of known specific devices that have been designed to prevent or treat carpal tunnel syndrome are various gloves, padding, splints and bandages. Davini U.S. Pat. No. 4,966,137 discloses a splint system consisting of rigid and elastic components applied circumferentially around the wrist. In theory, the device exerts a force to move the radius and ulna closer to each other and, therefore, reduce tension in the transverse carpal ligament to reduce compression of the median nerve.

Downes U.S. Pat. No. 5,413,553 describes a carpal tunnel mitt that is worn like a glove and through a strapping arrangement attempts to approximate the medial and lateral ends of the transverse carpal ligament and thereby reduce tension in the ligament and decompress the median nerve. It is questionable whether either of these devices can overcome the connective tissue forces to accomplish decompression.

Nirsch U.S. Pat. No. 4,441,490, Sebastian et al. U.S. Pat. No. 4,899,763, Nelson U.S. Pat. No. 4,584,993 and Meanchen et al. U.S. Pat. No. 5,014,689 all disclose splints that by various means immobilize the wrist. Maintaining the wrist in a neutral position and restricting movement is thought to minimize pressure in the carpal canal. This type of immobilization has not met with a high success rate and has the further disadvantage of limiting the user's mobility for work or other activities.

U.S. Pat. No. 5,031,640 discloses a pad for preventing carpal tunnel syndrome. This device consists of a padded surface that is interposed between a tool and the user's hand. While this device may lessen point pressure over the median nerve during tool use, it does not represent a device that can provide long term relief of carpal tunnel syndrome.

Fareed U.S. Pat. No. 5,441,058 discloses a device designed to provide circumferential pressure in the forearm area. This device could not be employed to effect dorsally directed force to the flexor tendons in the palm area.

Stoner U.S. Pat. No. 5,478,306 discloses a system for supporting carpals through providing circumferential pressure in the carpal area.

Sucher U.S. Pat. No. 5,468,220 discloses a device for applying a stretching force to the medial and lateral ends of the transverse carpal ligament. See also Sucher U.S. Pat. No. 5,256,136 which discloses stretching the transverse carpal ligament through positioning of the hand and thumb in an abducted position.

My co-pending U.S. patent application Ser. No. 08/826,778 discloses a device for stretching the intrinsic hand muscles and is generally adapted to be used during rest periods.

There remains, therefore, a very real and substantial need for an improved system for reducing median nerve compression in the carpal tunnel through applying a dorsally directed force in the palm region.

SUMMARY OF THE INVENTION

The present invention has met the above-described needs by providing an apparatus which will effectively resist the onset of carpal tunnel syndrome or minimize the effects thereof by a dorsally directed force to the palm of the hand. The apparatus may be worn while the user is engaging in activities.

In a first embodiment, the apparatus has an upper support which is structured to be secured in generally overlying relationship with respect to the hand. The upper support has a base in contact with the hand and strap supporting means which in one embodiment includes a pair of apertured towers through which a strap or straps may pass. A connecting bridge may be provided between the towers with the strap or straps secured thereto. It is preferred that the strap or straps be removably and adjustably secured as by use of hook and loop connectors such as that sold under the trade designation Velcro.

A palmar compression pad is structured to be in contact with the palm of the hand and have the strap means secured to adjacent ends thereof with the straps being in tension so as to be provide the generally dorsally directed force.

In one embodiment both the upper support and the palmar compression pad will be substantially rigid.

The method of the first embodiment of the present invention involves providing a palmar compression pad and securing the same to an upper support through strap means which are placed in sufficient tension so as to provide a generally dorsally directed force to the palm and thereby maintain the flexor tendon to the desired position so as to resist median nerve compression in the carpal tunnel.

In another embodiment of the invention a lower support or palmar compression pad may be generally rigid with ends which are structured to receive strap means of the upper support. The strap means is secured to a compressible, flexible upper support pad with the strap means placed in tension. The strap means may be secured to the palmar compression pad and to other portions of the strap means by hook and eye fastener means. The upper support may be flexible and compressible. The method of this embodiment involves providing an upper portion having strap means and a generally rigid lower support. The strap means are secured to the palmar compression pad to place the strap means in tension so as to apply through the palmar compression pad a dorsally directed force to the palm of the hand.

It is an object of the present invention to provide an apparatus and an associated method for the prevention and treatment of carpal tunnel syndrome.

It is a further object of the present invention to provide such a system which effects a generally dorsally directed force to the palmar region of the hand.

It is a further object of the present invention to provide such apparatus which may be applied by the user easily and rapidly to the hand.

It is a further object of the present invention to provide such a system which may be employed while the user goes about his or her ordinary daily activities.

It is another object of the present invention to provide such a system which is relatively small so as to not interfere with the user's general activities.

It is yet another object of the present invention to provide such a system which has adjustable strap means so as to facilitate achieving the desired level of tension.

These and other objects of the invention will be more fully understood from the following description of the invention with reference to the drawings appended hereto.

DESCRIPTION OF THE PREFERRED EMBODIMENTS

Figure 1:
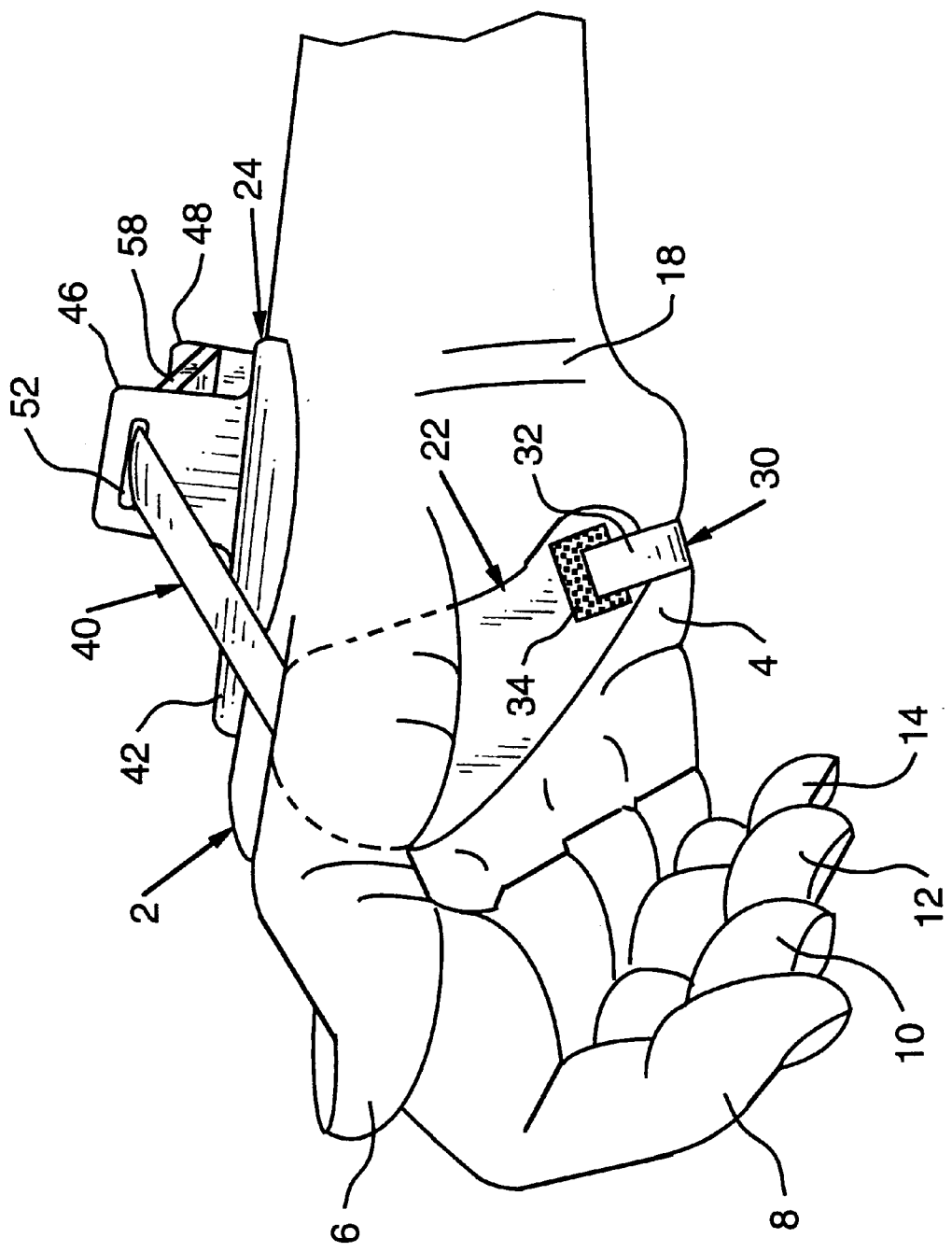
FIG. 1 is a perspective view of a user's hand showing the apparatus of the present invention secured to the hand.
Figures 2, 3:
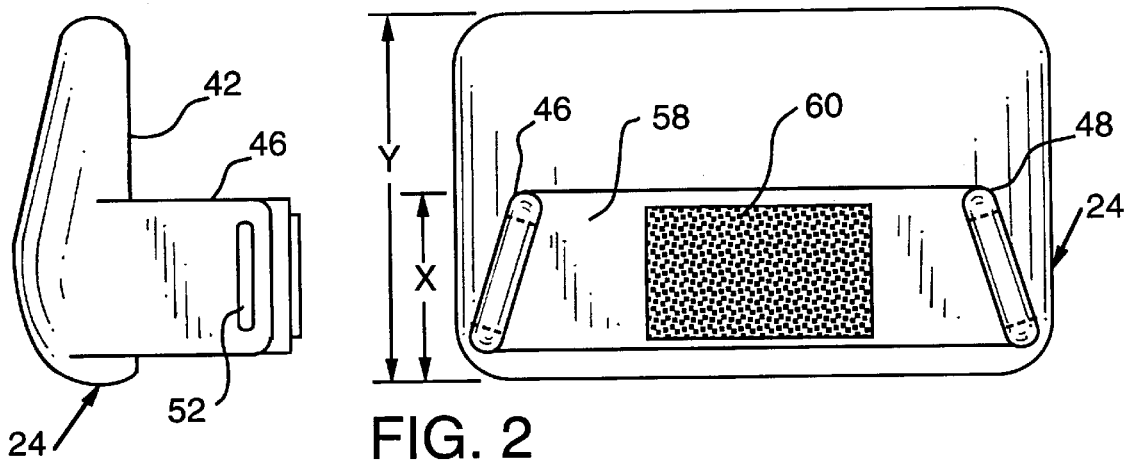
FIG. 2 is a top plan view of a form of upper support of the present invention.
FIG. 3 is a left side view of the upper support of FIG. 2.
Figure 4:
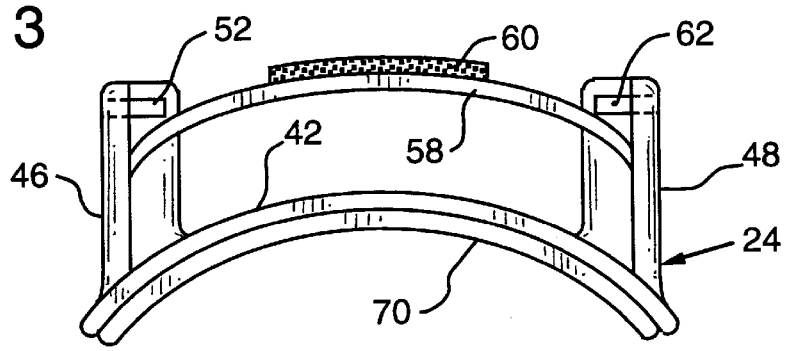
FIG. 4 is a front elevational view of the support of FIG. 2.

Referring again to FIG. 1, in a first embodiment, a user's hand 2 has a palm region 4, a thumb 6 and individual fingers or digits 8, 10, 12, 14 and a rearward hand portion 18 adjacent the wrist.

A palmar compression pad 22, which through straps 30, 40 cooperates with the upper support 24, is preferably substantially rigid and is secured within the palm region in intimate contact therewith and is preferably contoured so as to facilitate such intimate contact. The palmar compression pad 22 may be made of any suitable material such as a resinous plastic, rubber or metal as desired. In the form shown a pair of straps are secured adjacent opposed ends of the palmar compression pad 22. End 32 of strap 30 has hook or loop fastener means secured to hook or loop fastener means element 34 which is secured to palmar compression pad 22 to removably and adjustably secure the strap 30 to the palmar compression pad 22. A preferred form of hook and loop fastener means is that sold under the trade designation "Velcro." Similarly, while not shown in this view, strap 40 will have an end provided with hook or loop fastener means which are secured to a corresponding element secured to the palmar compression pad 22. When tension of a predetermined magnitude is applied to straps 30 and 40, the palmar compression pad 22 will provide a generally dorsally applied force to the palmar region of the hand and thereby maintain the flexor tendon in the desired dorsal position which in turn resists undesired median nerve compression in the carpal tunnel. This serves to prevent or resist the effects of carpal tunnel syndrome.

Referring to FIGS. 1 through 4, the upper support 24 will be considered in greater detail. In the form illustrated, the upper support portion has a base 42 which is preferably generally downwardly concave so as to facilitate comfortable positioning thereof in overlying relationship with respect to the dorsal region of the metacarpals. A pair of towers 46, 48 have apertures 52, 62 through which the straps 40, 30, respectively, will pass. The upper ends of the straps 40, 30 will be provided with hook or loop fastener means which are secured in adjustable and removable fashion to the corresponding hook or loop fastener element 60 which is secured to bridge 58 which connects towers 46, 48.

In the form shown, the towers 46, 48 are oriented generally angularly inwardly from the adjacent corners of the upper support 24. It will be appreciated that the towers 46, 48 and bridge 58 have a width X which is substantially less than the width Y of the base. The broader base enhances stability of the upper support 24 while the width X provides adequate width for effective support of the straps 30, 40.

In a preferred embodiment a pad 70 will be provided underlying the lower surface of the base 42 so as to provide more comfortable engagement with the hand 2. The upper support may advantageously be made of any suitable rigid material such as metal or a resinous plastic.

Figure 5:
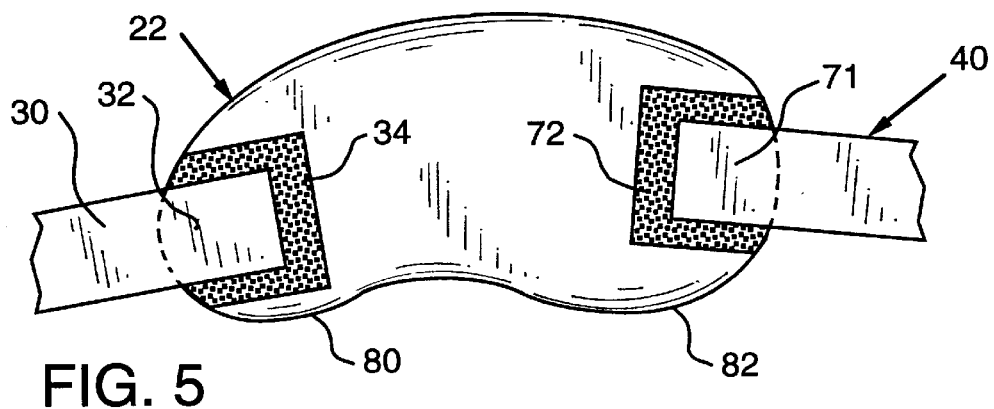
FIG. 5 is a fragmentary top plan view showing a form of palmar compression pad with straps attached thereto.
Figure 6:
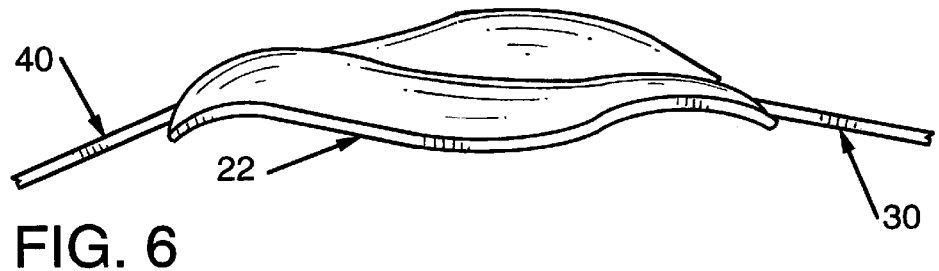
FIG. 6 is a fragmentary front elevational view of the palmar pad and associated straps of FIG. 5.

Referring to FIGS. 5 and 6, it will be appreciated that in the form shown the palmar compression pad 22 has strap end 32 secured thereto by cooperation between hook and loop fasteners secured to end 32 and element 34 secured to the palmar compression pad 22. Similarly, end 71 of strap 40 has underlying hook or loop fasteners which cooperate with complementary hook or loop fasteners on element 72 which is secured to the palmar compression pad 22. It will also be noted that the palmar compression pad 22 has an end 82 which is wider than the other end 80 so as to facilitate positioning of end 82 generally closer to the thumb as shown in FIG. 1.

As shown in FIG. 6, the palmar compression pad 22 is preferably having an irregular contoured surface so as to be of generally complementary shape with respect the central region of the palm of the hand and thereby facilitate intimate contact therebetween.

In effecting securement of the apparatus of the present invention to the hand, the straps 30, 40 will have their upper ends secured to fastening element 60. The upper support 24 will then be positioned in the desired location in contact with the upper portion of the hand with one of the ends of straps 30, 40 being preapplied to the palmar compression pad 22. The palmar compression pad 22 is then positioned in the desired location and the other strap is pulled to the desired tension after which it is secured in that position. The device may be worn in this position for any desired period of time.

While it will be appreciated that a pair of straps 30, 40 have been shown in the first embodiment illustrated, if desired a single strap could be employed with the fastening means provided at the free ends of the strap and support being provided by the upper support with or without apertured towers so long as adequate restraint is provided by the upper support. Also, other fastening means such as adjustable belts having discrete positions as a result of specific apertures through which a metal tongue would pass can be employed. One of the advantages of the present strap approach is that the positioning is continuously variable to thereby permit precise tension to be applied regardless of hand size.

The straps 30, 40, 120 may be flexible, but generally not extensible or, in the alternative, may be elastic so as to enhance the applied tension. In the method of the present invention applying the upper support 24 and the palmar compression pad 22 with the straps serving to provide the desired tension creates the desired generally dorsally directed force on the palm of the hand to position the flexor tendon in the desired location and thereby reduce undesired median nerve compression within the carpal tunnel.

Figure 7:
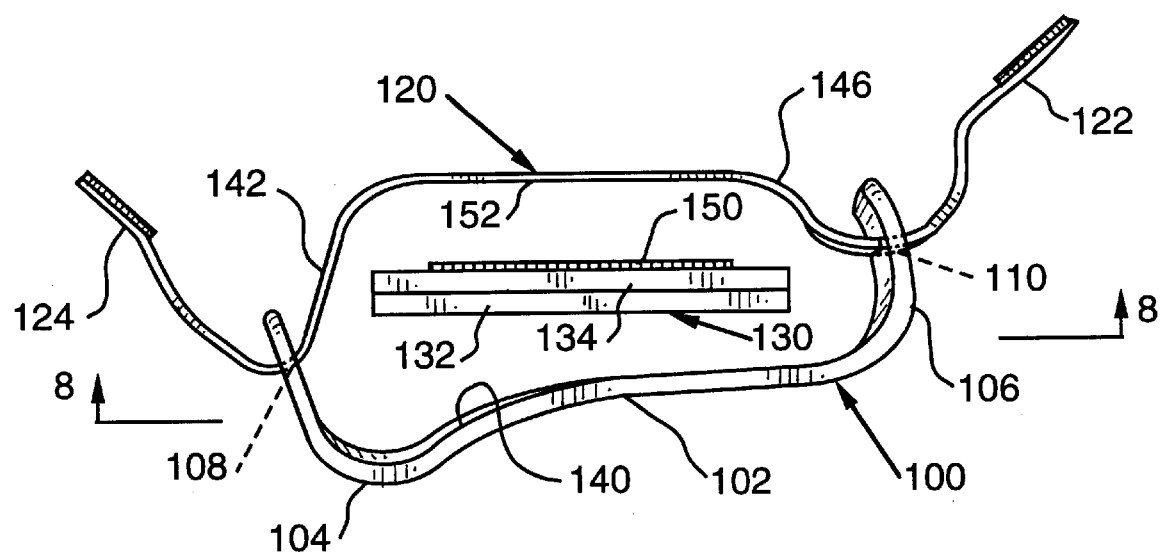
FIG. 7 is an exploded schematic view of another embodiment of the apparatus of the present invention.
Figure 8:
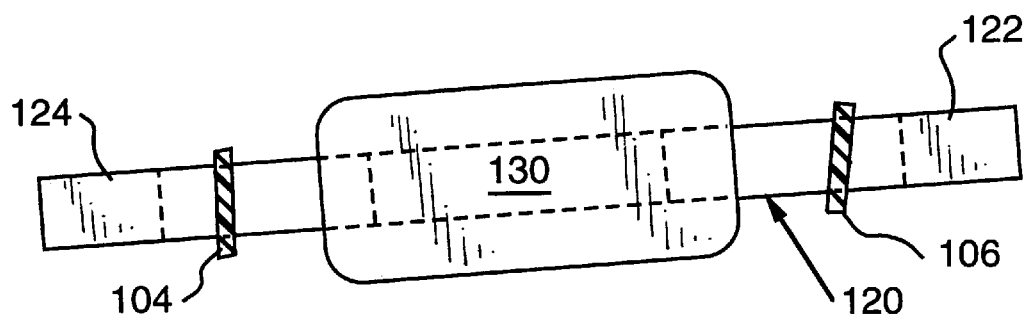
FIG. 8 is a cross-sectional view taken through 8—8 of FIG. 7.

Referring to FIGS. 7 and 8, the lower support or palmar compression pad 100 is generally rigid and has, in the form shown, a downwardly convex portion 102 and a pair of generally upwardly projecting legs 104, 106 which have, respectively, openings 108, 110. The palmar compression pad or the lower support 100 may conveniently be made of a generally rigid plastic, but may have a degree of flexibility to permit it to conform to the palm of the hand. As employed herein, the reference to the palmar compression pad or lower support being "substantially rigid" shall refer to a material which is generally rigid and not resiliently compressible which may be in the form of an article which has a limited degree of flexibility, but will retain its shape when it is not subjected to deforming forces. The palmar compression pad 100, in the form shown, is generally U-shaped. Flexible strap means 120 have ends 122, 124 passing, respectively, through openings 110, 108 and as will be described hereinafter, are adapted to be secured to other portions of the strap when securing the assembly in use.

The upper support 130, in the preferred form shown, has a lower resiliently compressible layer 132 which may be composed of a resiliently compressible resinous foam material. The upper layer 134 of the upper support 130 in a preferred embodiment is a stiffening web of a resinous plastic material 134. The assembly of layer 132 and web 134 may be created by gluing. It will be appreciated that in this manner the lower portion 132 will contact the upper surface of the hand of the user and the upper surface 140 of the lower portion will contact the palm 164 of the hand 160. In a preferred embodiment of the invention, hook and loop-type fasteners such as that marketed under the trade designation "Velcro," are provided on the strap means 120, such that ends 124, 122 can be secured to strap portions 142, 146 after the belt has been placed under the desired tension. Similarly, secured to the upper surface of the upper support 130 is a layer of hook and loop fastener 150 which secures to portion 152 of the strap 120.

Figure 9:
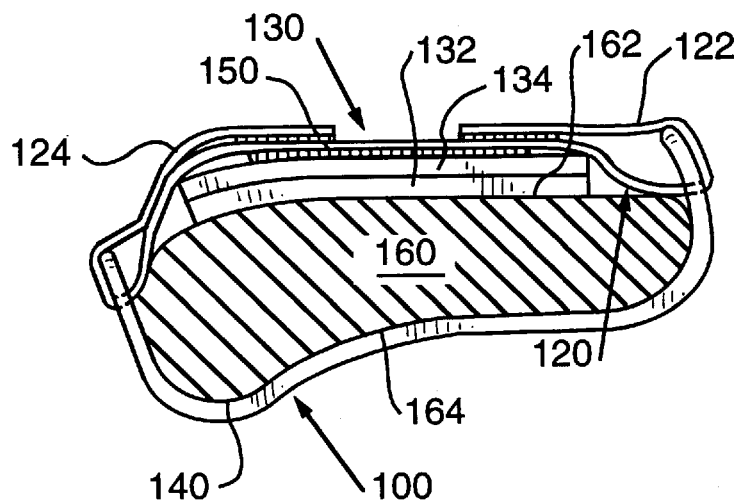
FIG. 9 is a schematic illustration of the embodiment of FIG. 7 shown in contact with a user's hand.
Figure 10:
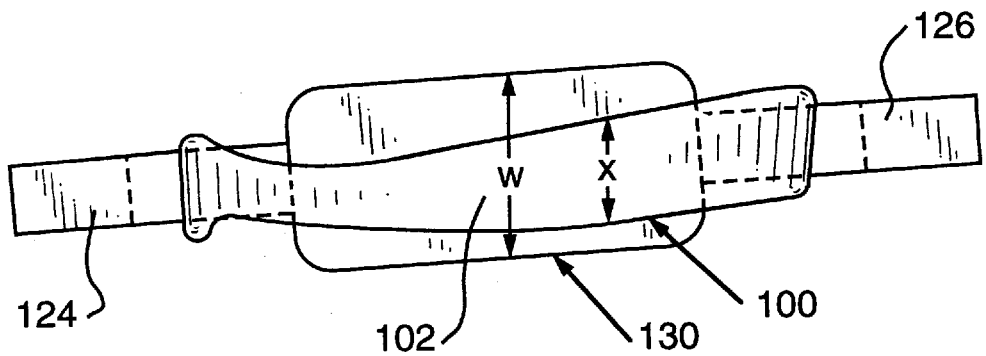
FIG. 10 is a bottom plan view showing a portion of the assembly of the embodiment of FIG. 7.
Figure 11:
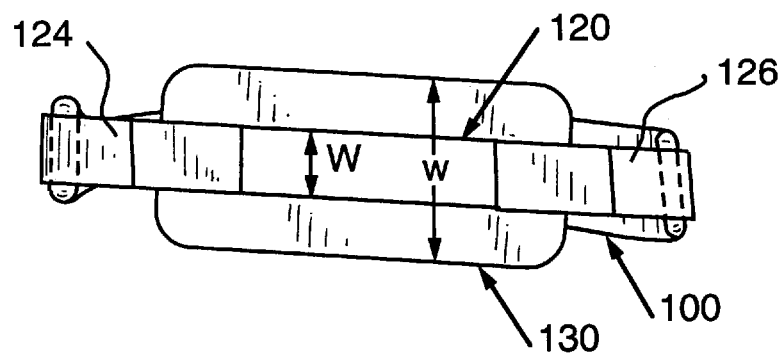
FIG. 11 is a top plan view of the complete assembly of the embodiment of FIG. 7.

Referring to FIG. 9, there is shown schematically a hand 160 having an upper portion 162 and a palm 164. The palmar compression pad 100 is shown as intimately engaging the palm 164 of the hand. The upper support 130 is secured in underlying relationship with respect to the strap means 120. By applying suitable tension to the strap 120 and having ends 124, 122 reentrantly configured and secured to other portions of the strap 120, there is applied through the palmar compression pad 100 a dorsally directed force to the palm 164 of the person's hand by the upper portion of the palmar compression pad 100 and the projecting strap means 124, 126. As shown, in the bottom plan view of FIG. 11, the strap means, which in the form shown, is a single elongated flexible strap means 120 has a width W less than the width w of upper support 130. As shown in FIG. 10, the average width x of the palmar compression pad 100 is less than width w of upper support 130.

While in the preferred form shown a single strap has been employed, in view of the Velcro securement of the strap 120 to the upper surface of the upper support, a pair of straps could be employed with one end of each strap being secured to the upper surface of the upper support and the other end being reentrantly folded and secured to a portion of the strap.

While in the preferred form, the upper support 130 is flexible to facilitate efficient application of the dorsally directed force, it could be rigid or substantially rigid, if desired.

It will be appreciated, therefore, that the present invention provides an effective system for resisting the onset of carpal tunnel syndrome and reducing the consequences of carpal tunnel syndrome. This is accomplished by providing a palnar compression pad which is placed under tension as a result of strap or straps which may be totally or partially elastic. The straps are secured to an upper support which maintains the desired tension on the palmar compression pad. The apparatus is of sufficiently small size that it may be worn on an ongoing basis even though the individual using the same is going about his or her normal activities.

Whereas particular embodiments of the invention have been described herein for purpose of illustration, it will be evident to those skilled in the art that numerous variations of the details may be made without departing from the invention as defined in the appended claims.

What is claimed is:

1. A hand orthosis for applying a generally dorsally directed force to the palm of the hand comprising:

(a) an upper support structured to be in contact with an upper surface of the hand opposite the palm of the hand and secured in overlying contacting relationship with respect to the dorsal region of the metacarpals;

(b) a generally rigid unitary palmar compression pad structured to be in contact with the palm of the hand, the palmar compression pad having a pair of strap engaging ends and an irregular contoured surface sized and configured to generally complement the shape of the central region of the palm; and (c) flexible strap means secured to said palmar compression pad and to said upper support for applying the dorsally directed force solely to the palmar region of the hand and not the wrist, whereby said orthosis is sized and configured to only apply said dorsally directed force to the central palmar region of the hand thereby maintaining the flexor tendon in a desired dorsal position.

2. The apparatus of claim 1 including said strap engaging ends having openings for passage of said strap means therethrough.

3. The apparatus of claim 2 including
said strap means being detachably securable to at least one of said palmar compression pad and said upper support.

4. The apparatus of claim 1 including
said strap means being detachably securable to both said palmar compression pad and said upper support.

5. Apparatus for applying a generally dorsally directed force to the palm of a person's hand comprising
an upper support structured to be in contact with an upper surface of the hand opposite the palm of the hand and secured in overlying contacting relationship with respect to the dorsal region of the metacarpals
a generally rigid palmar compression pad structured to be in contact with the palm of the hand,
said palmar compression pad having a pair of strap engaging ends,
flexible strap means securable to said palmar compression pad and to said upper support for applying the dorsally directed force solely to the hand, whereby said dorsally directed force will not be applied to the wrist,
said strap engaging ends having openings for passage of said strap means therethrough, and
said palmar compression pad strap engaging ends projecting generally upwardly from a convex portion of said palmar compression pad.

6. The apparatus of claim 5 including
said palmar compression pad being of generally U-shape.

7. The apparatus of claim 5 including said strap means having a strap with ends passing through said openings and securable to said upper support and to other portions of said strap means.

8. The apparatus of claim 7 including
said strap means being secured to said palmar compression pad and to other portions of said strap by hook and loop fastener means, whereby securing said strap means in tension will apply a generally dorsally directed force to said palm.

9. The apparatus of claim 5 including
said upper support having a greater average width than the average width of said strap means.

10. Apparatus for applying a generally dorsally directed force to the palm of a person's hand comprising
an upper support structured to be secured in generally overlying contacting relationship with respect to the dorsal region of the metacarpals,
a generally rigid palmar compression pad structured to be in contact with the palm of the hand,
said palmar compression pad having a pair of strap engaging ends,
flexible strap means securable to said palmar compression pad and to said upper support for applying the dorsally directed force,
said strap engaging ends having openings for passage of said strap means therethrough
said palmar compression pad strap engaging ends projecting generally upwardly from a convex portion of said palmar compression pad, and
said upper support being generally flexible.

11. The apparatus of claim 10 including
said upper support being resiliently compressible.

12. A method of reducing median nerve compression in the carpal canal comprising
providing a palmar compression pad positioned on the back surface of the hand and an upper support with strap means supported by said upper support and adjustably secured to said palmar compression pad,
said palmar compression pad being generally rigid, positioning said palmar compression pad in intimate contact with the palm of the user, and
securing said strap means in tension to said palmar compression pad and said upper support to thereby cause a generally dorsally directed force to be applied to said palm whereby the dorsally directed force reduces the median nerve compression in the carpal canal.

13. The method of claim 12 including
securing said strap means to an upper side of said upper portion.

14. The method of claim 13 including
employing hook and loop fasteners to secure said strap means to said upper support.

15. The method of claim 12 including
employing as said strap means a strap having end portions secured to other portions of said strap with said strap in tension.

16. A method of reducing median nerve compression in the carpal canal comprising
providing a palmar compression pad positioned on the back surface of the hand and an upper support with strap means supported by said upper support and adjustably secured to said palmar compression pad,
said palmar compression pad being generally rigid,
positioninig said palmar compression pad in intimate contact with the palm of the user,
securing said strap means in tension to said palmar compression pad and said upper support to thereby cause a generally dorsally directed force to be applied to said palm,
securing said strap means to an upper side of said of upper support,
employing hook and loop fasteners to secure said strap means to said upper support
providing said palnar compression pad with a pair of generally upwardly extending legs having strap receiving openings, and
passing said strap means through said openings and securing said strap means in tension.

17. The method of claim 16 including
securing said strap means to said upper support by hook and loop fasteners.

18. The method of claim 17 including
employing as said upper support a flexible, compressible pad.

* * * * *